US00PP11694P

United States Patent [19]

Klemm

[11] Patent Number: Plant 11,694

[45] Date of Patent: Dec. 12, 2000

[54] NEW GUINEA IMPATIENS PLANT NAMED 'DELHI'

[75] Inventor: Siegfried Klemm, Stuttgart, Germany

[73] Assignee: Klemm & Sohn, Stuttgart, Germany

[21] Appl. No.: 09/213,443

[22] Filed: Dec. 17, 1998

[51] Int. Cl.[7] ..... A01H 5/00

[52] U.S. Cl. ..... Plt./318

[58] Field of Search ..... Plt./318

*Primary Examiner*—Howard J. Locker
*Assistant Examiner*—Michelle Kizilkaya
*Attorney, Agent, or Firm*—C. A. Whealy

[57] ABSTRACT

A new and distinct cultivar of New Guinea Impatiens plant named 'Delhi', characterized by its numerous large crimson red-colored flowers that are held above the foliage; uniform and rounded growth habit; medium plant height; very freely branching, dense and bushy plant habit; and dark green leaves.

1 Drawing Sheet

BACKGROUND OF THE INVENTION

The present invention relates to a new and distinct cultivar of New Guinea Impatiens plant, botanically known as *Impatiens hawkeri*, and herinafter referred to by the cultivar name Delhi.

The new cultivar is a product of a planned breeding program conducted by the Inventor in Stuttgart, Germany. The objective of the breeding program was to develop varieties with good branching, medium plant height, rounded plant habit, early flowering, floriferousness, bright flower color, and large round flowers.

The new cultivar originated from a cross made by the Inventor of the New Guinea Impatiens selection identified as A 069, not patented, as the male, or pollen parent, with the New Guinea Impatiens selection identified as N 295, not patented, as the female, or seed parent.

The cultivar Delhi was discovered and selected by the Inventor in 1996 as a flowering plant within the progeny of the stated cross in a controlled environment in Stuttgart, Germany.

Asexual reproduction of the new cultivar by terminal cuttings taken at Stuttgart, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Delhi'. These characteristics in combination distinguish 'Delhi' as a new and distinct cultivar:

1. Numerous large crimson red-colored flowers that are held above the foliage.
2. Uniform and rounded growth habit.
3. Medium plant height.
4. Very freely branching, dense and bushy plant habit.
5. Dark green leaves.

Compared to plants of the male parent, the crimson-red selection identified as A 069, plants of the new Impatiens have a redder flower color and flower earlier. Compared to plants of the female parent, the violet selection identified as N 295, plants of the new Impatiens differ in flower color, are larger, have larger flowers and leaves, and are more uniform.

Plants of the new Impatiens are similar in flower color to plants of the nonpatented New Guinea Impatiens cultivar Kamina. However, in side-by-side comparisons conducted in Stuttgart, Germany, plants of the new Impatiens had a more uniform plant habit and larger flowers than plants of the cultivar Kamina.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'Delhi'. Flower and foliage colors in the photographs may differ from the actual colors due to lifht reflectance.

DETAILED BOTANICAL DESCRIPTION

Plants of the cultivar Delhi have not been observed under all possible environmental conditions. The phenotype may vary somewhat with variations in environment such as temperature and light intensity, without, however, any variance in genotype. The following observations, measurements and comparisons describe plants grown in Stuttgart, Germany, under greenhouse and outdoor production practices.

In the following description, color references are made to The Royal Horticultural Society Colour Chart except where general terms of ordinary dictionary significance are used.

Classification:

*Botanical.*—*Impatiens hawkeri* cultivar Delhi.

*Commercial.*—New Guinea Impatiens cultivar Delhi.

Parentage:

*Male parent.*—*Impatiens hawkeri* selection identified as A 069.

*Female parent.*—*Impatiens hawkeri* selection identified as N 295.

Propagation:

*Type cutting.*—Terminal cuttings.

*Time to initiate and develop roots.*—About 16 days.

Plant Description:

*Crop time (precocity).*—From rooted cuttings to flowering about 80 to 90 days are required.

*Plant form.*—Uniform and rounded growth habit, plants appear almost spherical; upright yet spreading.

*Growth habit.*—Moderately vigorous. Very freely branching, dense and bushy growth. Appropriate for 10 to 25-cm containers.

*Plant size.*—Height, about 16.5 cm; spread, about 29.5 cm.

*Lateral stems.*—Quantity: About 11 basal branches; each basal branch with about 3 to 4 lateral stems. Length: About 16.5 cm.

*Foliage description.*—Medium-sized leaves; simple, generally symmetrical, moderate in quantity, opposite or in whorls, usually flat. Shape: Oblong-lanceolate to lanceolate; margin, shallow serration. Texture: Smooth. Color: Upper surface: 147A; venation, 145C. Lower surface: 138C; venation, 184B. Petiole length: About 2 cm.

Flower description:

*Flower type and habit.*—Large scarlet-colored flowers. Early and freely flowering; usually about 30 flowers per plant. Single flowers arranged in clusters arising from leaf axils. Flowers positioned above the foliage and face upward and outward. Flower shape is rounded. Flowers not persistent.

*Flowering season.*—Year-round under greenhouse conditions. In the garden, flowering is continuous from spring until fall.

*Flower longevity.*—About 10 to 14 days on the plant; about 1 to 2 days as a cut flower.

*Flower size.*—Diameter: About 6.8 cm. Depth: About 1 cm.

*Flower buds.*—Length: About 1.2 cm. Diameter: About 7 mm. Shape: Ovoid. Color: 63A.

*Petals.*—Quantity: Five. Shape: Cordate with acute base and entire margin. Texture: Satiny, smooth. Color: Fully opened, upper surface: Red purple, 57B; base or "eye", 46A. Color may fade slightly with subsequent development. Fully opened, lower surface: 46C.

*Sepals.*—Three, lower sepal spurred. Color, lateral sepals: Inside: 138C. Outside: Adaxial, 66C; abaxial, 138C. Color, spurred sepal: Inside: 66C. Outside: 66C.

*Peduncles.*—Length: About 5.3 cm. Angle: About 35° to stem. Strength: Stiff, strong. Color: Grayed-purple.

*Reproductive organs.*—Androecium: Stamen number: Five, anthers fused, filaments free. Anther shape: Obovate. Pollen color: Cream. Gynoecium: Five-loculate fused. Style length: About 4 mm. Style color: Green. Stigma color: Cream.

*Fruit.*—Green, pulpy explosive capsule.

*Seed.*—Brown, about 2 to 3 mm in length.

Disease resistance: Under commercial conditions, good to moderate resistance to Botrytis has been observed.

It is claimed:

1. A new and distinct cultivar of New Guinea Impatiens plant named 'Delhi', as illustrated and described.

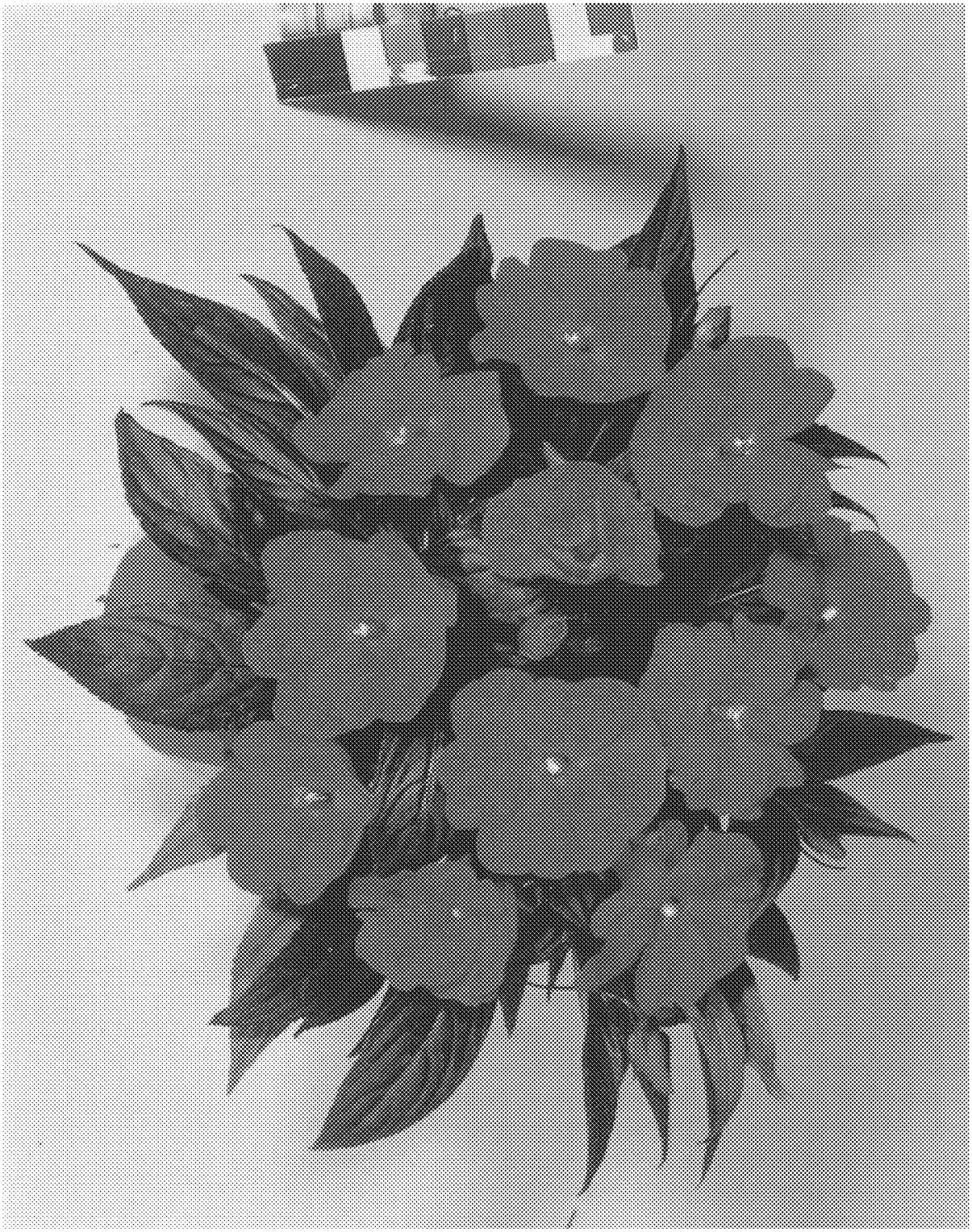

* * * * *